US012600797B2

(12) United States Patent
Matsumura et al.

(10) Patent No.: US 12,600,797 B2
(45) Date of Patent: *Apr. 14, 2026

(54) FIBRIN-BINDING ANTIBODY AND PHARMACEUTICAL COMPOSITION CONTAINING ANTIBODY

(71) Applicants: NATIONAL CANCER CENTER, Tokyo (JP); RIN INSTITUTE INC., Tokyo (JP)

(72) Inventors: Yasuhiro Matsumura, Chiba (JP); Shingo Hanaoka, Chiba (JP); Shinji Saijo, Chiba (JP)

(73) Assignees: RIN INSTITUTE INC., Tokyo (JP); NATIONAL CANCER CENTER, Tokyo (JP)

( * ) Notice: Subject to any disclaimer, the term of this patent is extended or adjusted under 35 U.S.C. 154(b) by 818 days.

This patent is subject to a terminal disclaimer.

(21) Appl. No.: 17/915,885

(22) PCT Filed: Mar. 30, 2021

(86) PCT No.: PCT/JP2021/013512
§ 371 (c)(1),
(2) Date: Sep. 29, 2022

(87) PCT Pub. No.: WO2021/200932
PCT Pub. Date: Oct. 7, 2021

(65) Prior Publication Data
US 2023/0132177 A1 Apr. 27, 2023

(30) Foreign Application Priority Data
Mar. 31, 2020 (JP) ................................. 2020-061975

(51) Int. Cl.
*C07K 16/36* (2006.01)
*A61P 35/00* (2006.01)

(52) U.S. Cl.
CPC .............. *C07K 16/36* (2013.01); *A61P 35/00* (2018.01); *C07K 2317/24* (2013.01); *C07K 2317/565* (2013.01)

(58) Field of Classification Search
None
See application file for complete search history.

(56) References Cited

U.S. PATENT DOCUMENTS

| | | |
|---|---|---|
| 8,877,195 B2 | 11/2014 | Akassoglou |
| 9,429,584 B2 * | 8/2016 | Matsumura ........ A61K 47/6843 |
| 11,311,626 B2 * | 4/2022 | Matsumura ........ A61K 47/6843 |
| 2012/0183560 A1 | 7/2012 | Akassoglou |
| 2016/0011217 A1 | 1/2016 | Matsumura et al. |
| 2020/0147231 A1 | 5/2020 | Matsumura et al. |

FOREIGN PATENT DOCUMENTS

| | | | |
|---|---|---|---|
| EP | 3620471 A1 | 3/2020 | |
| TW | 201842938 A | 12/2018 | |
| WO | WO-2011/158973 A1 | 12/2011 | |
| WO | WO-2014133093 A1 * | 9/2014 | ........ A61K 47/6843 |
| WO | WO-2016/167227 A1 | 10/2016 | |
| WO | WO-2018203517 A1 * | 11/2018 | ............ C07K 16/36 |

OTHER PUBLICATIONS

Dvorak et al., "Chapter 57: Malignancy and Hemostasis." *Hemostasis and Thrombosis: Basic Principles and Clinical Practice, Fifth Edition.* Colman et al., Eds., Lippincott Williams & Wilkins, 851-873 (2006) (25 pages).
Dvorak, "Vascular permeability factor/vascular endothelial growth factor: a critical cytokine in tumor angiogenesis and a potential target for diagnosis and therapy," J. Clin. Oncol. 20:4368-80 (Nov. 2002).
Matsumura, "Cancer and Blood Coagulation." *Cancer Drug Delivery Systems Based on the Tumor Microenvironment.* Yasuhiro Matsumura and David Tarin, Eds., 23-40 (2019) (12 pages).
Office Action dated Aug. 17, 2024, for Chinese Patent Application No. 202180025986.6, Matsumura et al., "Fibrin-binding Antibody and Pharmaceutical Composition Containing Same," filed Mar. 30, 2021 (4 pages).
Office Action dated Feb. 23, 2024, for Chinese Patent Application No. 202180025986.6, Matsumura et al., "Fibrin-binding antibody and pharmaceutical composition containing same," filed Mar. 30, 2021 (8 pages).
Office Action dated Sep. 5, 2024, for Taiwanese Patent Application No. 110111843, Matsumura et al., "Fibrin-binding antibody and pharmaceutical composition containing antibody," filed Mar. 31, 2021 (6 pages).
International Search Report mailed Apr. 27, 2021 for International Application No. PCT/JP2021/013512, Matsumura et al., "Fibrin-Binding Antibody and Pharmaceutical Composition Containing Antibody," filed Mar. 30, 2021 (English translation) (5 pages).
Matsumura, "Cancer Stromal Targeting Therapy," Yakugaku Zasshi 137(5):529-534 (2017) (English translation) (13 pages).
Extended European Search Report dated Feb. 2, 2024, for European Patent Application No. 21780242.0, Matsumura et al., "Fibrin-Binding Antibody and Pharmaceutical Composition Containing Antibody," filed Mar. 30, 2021 (9 pages).
Fuchigami et al., "Chemotherapy payload of anti-insoluble fibrin antibody-drug conjugate is released specifically upon binding to fibrin," Sci Rep. 8(1):14211 (Sep. 2018) (9 pages).

* cited by examiner

*Primary Examiner* — Michael Szperka
(74) *Attorney, Agent, or Firm* — Clark & Elbing LLP

(57) ABSTRACT
The present invention provides an antibody that binds to fibrin and a pharmaceutical composition containing the antibody. According to the present invention, there is particularly provided a humanized antibody that binds to fibrin and a pharmaceutical composition containing the antibody.

7 Claims, 5 Drawing Sheets
Specification includes a Sequence Listing.

Pancreatic tissue slice of HE-PKC mouse

| Humanized 1101 antibody | Humanized 99 antibody |
|---|---|

10 µg/mL          10 µg/mL

1 µg/mL          1 µg/mL

Arrow indicates blood clot

Humanized 1101 antibody 0.5 μg/ml

Humanized 1101 antibody 0.2 μg/ml

Humanized 99 antibody 0.5 μg/ml

Humanized 99 antibody 0.2 μg/ml

FIBRIN-BINDING ANTIBODY AND PHARMACEUTICAL COMPOSITION CONTAINING ANTIBODY

SEQUENCE LISTING

The instant application contains a Sequence Listing which has been submitted electronically in ASCII format and is hereby incorporated by reference in its entirety. Said ASCII copy, created on Sep. 27, 2022, is named 51021_018001_Sequence_Listing_9_27_22_ST25 and is 9,975 bytes in size.

TECHNICAL FIELD

The present invention relates to a fibrin-binding antibody and a pharmaceutical composition containing the antibody.

BACKGROUND ART

Antibodies that bind to fibrin with a stronger affinity than to fibrinogen have been developed (Patent Literatures 1 and 2). These Patent Literatures disclose that the antibodies are used for cancer treatment. An antibody strongly that binds to fibrin can also be used in-vivo imaging (Patent Literatures 1 and 2).

CITATION LIST

Patent Literatures

Patent Literature 1: WO2014/133093
Patent Literature 2: WO2018/203517

SUMMARY OF INVENTION

The present invention provides an antibody that binds to fibrin and a pharmaceutical composition containing the antibody. The present invention particularly provides a humanized antibody that binds to fibrin and a pharmaceutical composition containing the antibody.

According to the present invention, the following inventions are provided.

[1] An antibody that binds to insoluble fibrin or an antigen-binding fragment thereof, comprising (1) a heavy chain variable region comprising heavy chain CDR1 having an amino acid sequence set forth in SEQ ID NO:1, heavy chain CDR2 having an amino acid sequence set forth in SEQ ID NO:2 and heavy chain CDR3 having an amino acid sequence set forth in SEQ ID NO:3, and a light chain variable region comprising light chain CDR1 having an amino acid sequence set forth in SEQ ID NO:4, light chain CDR2 having an amino acid sequence set forth in SEQ ID NO:5 and Light chain CDR3 having an amino acid sequence set forth in SEQ ID NO:6; or (2) a heavy chain variable region comprising heavy chain CDR1 having an amino acid sequence set forth in SEQ ID NO:9, heavy chain CDR2 having an amino acid sequence set forth in SEQ ID NO:10 and heavy chain CDR3 having an amino acid sequence set forth in SEQ ID NO:11, and a light chain variable region comprising light chain CDR1 having an amino acid sequence set forth in SEQ ID NO:12, light chain CDR2 having an amino acid sequence set forth in SEQ ID NO:13 and light chain CDR3 having an amino acid sequence set forth in SEQ ID NO:14.

[2] An antibody that binds to insoluble fibrin or an antigen-binding fragment thereof, comprising (3) a heavy chain variable region having an amino acid sequence set forth in SEQ ID NO:7 and a light chain variable region having an amino acid sequence set forth in SEQ ID NO:8; or (4) a heavy chain variable region having an amino acid sequence set forth in SEQ ID NO:15 and a light chain variable region having an amino acid sequence set forth in SEQ ID NO:16.

[3] The antibody that binds to insoluble fibrin or an antigen-binding fragment thereof according to [1] or [2], wherein the antibody binds to insoluble fibrin with a stronger affinity than to fibrinogen or binds to insoluble fibrin with a stronger affinity than to fibrinogen, and comprises (5) a heavy chain variable region having an amino acid sequence having an identity of 90% or more to the heavy chain variable region of the antibody described in any one of the above (1) to (4) and the light chain variable region of the antibody, (6) the heavy chain variable region of the antibody described in any one of the above (1) to (4) and a light chain variable region having an amino acid sequence having an identity of 90% or more to the light chain variable region of the antibody, (7) a heavy chain variable region having an amino acid sequence having an identity of 90% or more to the heavy chain variable region of the antibody described in any one of the above (1) to (4) and a light chain variable region having an amino acid sequence having an identity of 90% or more to the light chain variable region of the antibody, (8) a heavy chain variable region having an amino acid sequence having an identity of 95% or more to the heavy chain variable region of the antibody described in any one of the above (1) to (4) and the light chain variable region of the antibody, (9) the heavy chain variable region of the antibody described in any one of the above (1) to (4) and a light chain variable region having an amino acid sequence having an identity of 95% or more to the light chain variable region of the antibody, or

(10) a heavy chain variable region having an amino acid sequence having an identity of 95% or more to the heavy chain variable region of the antibody described in any one of the above (1) to (4) and a light chain variable region having an amino acid sequence having an identity of 95% or more to the light chain variable region of the antibody.

[4] The antibody or an antigen-binding fragment thereof according to any one of [1] to [3], which is a humanized antibody or an antigen-binding fragment thereof.

[5] An antibody-drug conjugate comprising the antibody or an antigen-binding fragment thereof according to any one of [1] to [4].

[6] A pharmaceutical composition comprising the antibody-drug conjugate according to [5].

[7] The pharmaceutical composition according to [6], for use in treating a cancer.

[8] A pharmaceutical composition for use in treating a cancer, comprising an anti-cancer agent comprising the antibody or an antigen-binding fragment thereof according to any one of [1] to [4].

[9] An in-vivo diagnostic agent comprising the antibody or an antigen-binding fragment thereof according to any one of [1] to [4].

Figure 2:
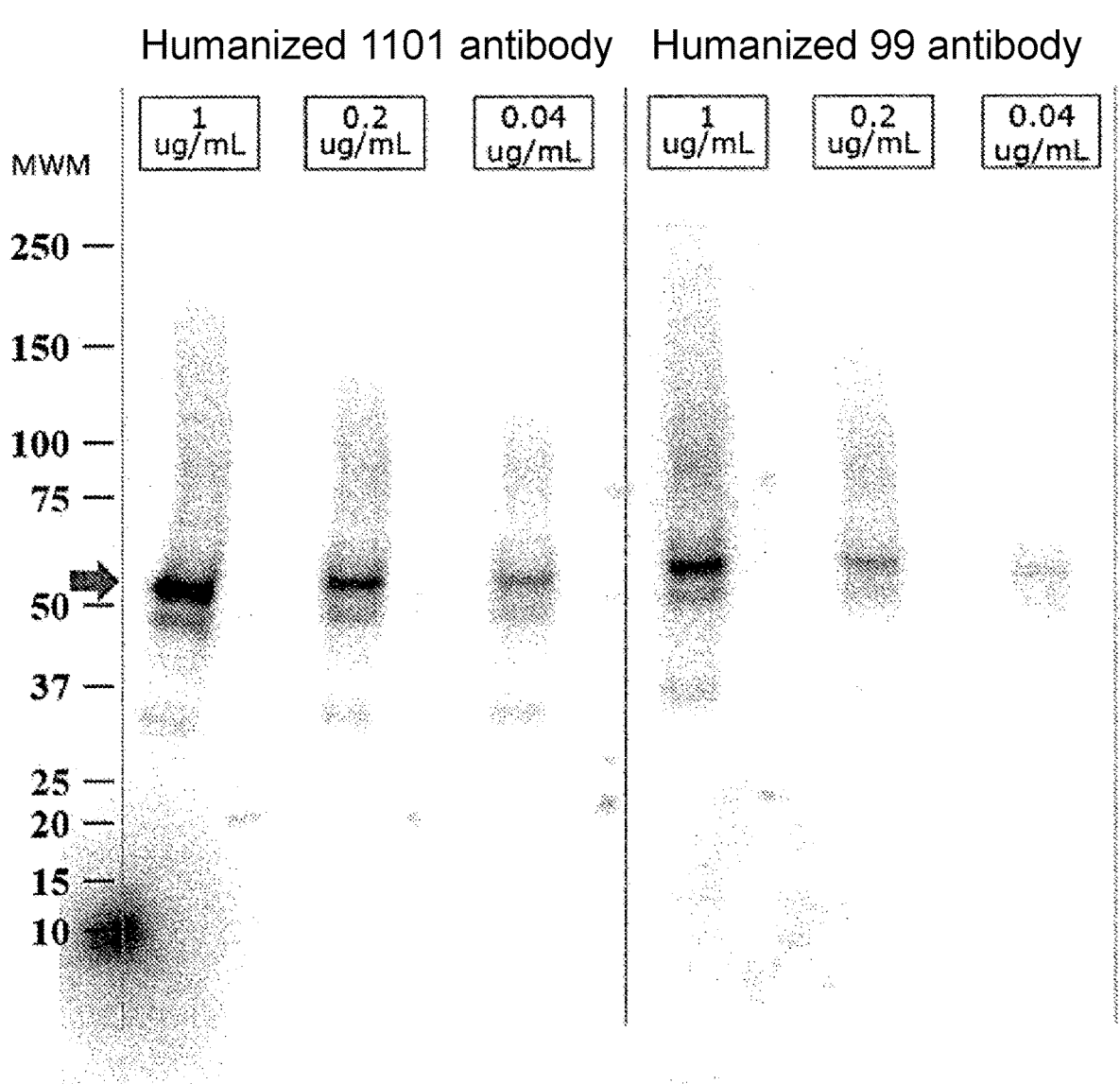

FIG. 2 shows western blot results showing reactivities of antibodies to denatured fibrinogen (1 µg/lane). Denatured fibrinogen was subjected to SDS-PAGE, transferred to a membrane, and then, antibodies having concentrations shown in the figure were allowed to react to the membrane. The denatured fibrinogen has a structure (non-denatured fibrinogen does not have), which is characteristic to insoluble fibrin, and to which humanized 99 and 1101 antibodies bind.

Figure 3:
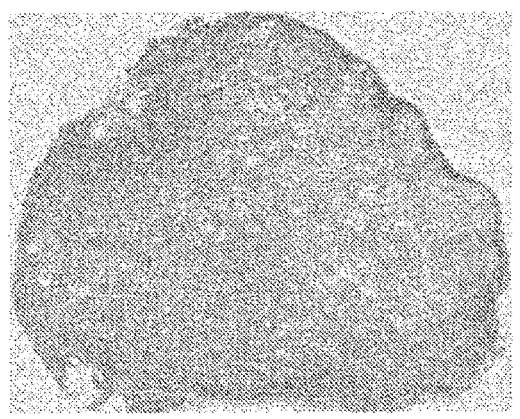
Figure 3:
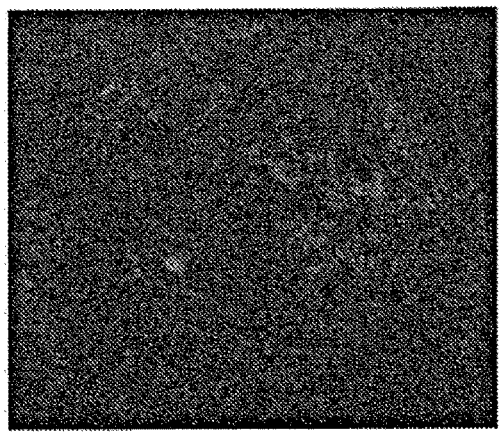
Figure 3:
Figure 3:
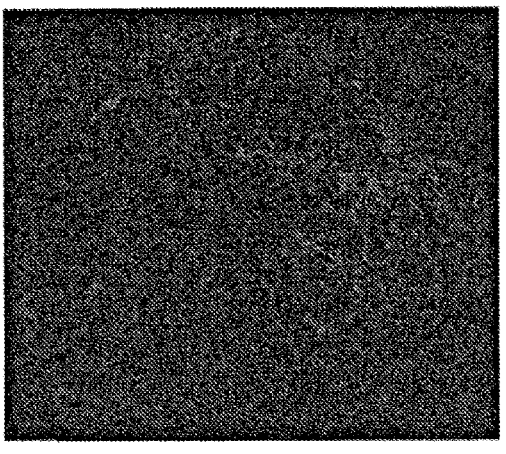
Figure 3:
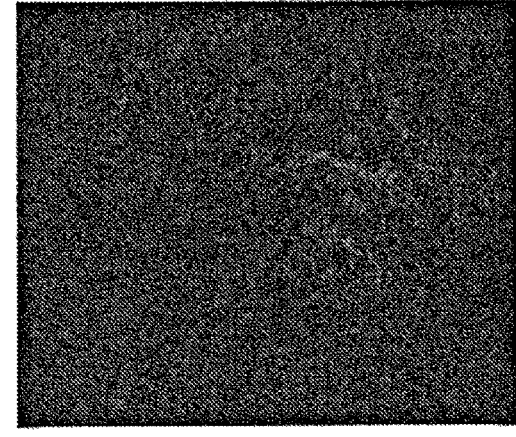

FIG. 3 shows an image (top panel) of a tissue section of the pancreas taken from HE-PKC mouse and stained with hematoxylin-eosin and images (4 panels in the lower stage) of the pancreatic tissue section immunohistochemically stained with humanized 1101 antibody and humanized 99 antibody.

Figure 4:
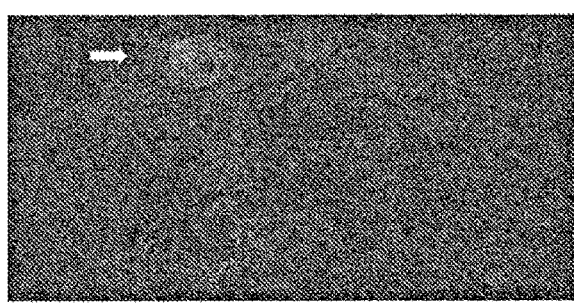
Figure 4:
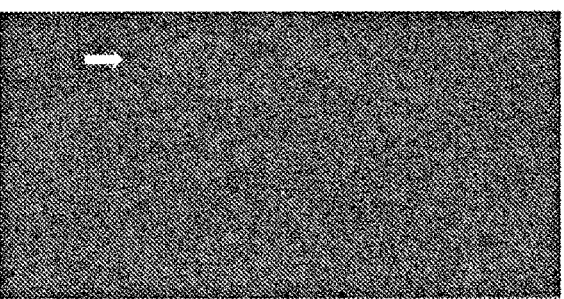
Figure 4:
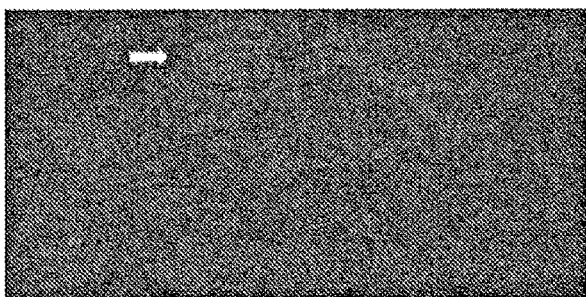

FIG. 4 shows images of blood clot (which coincidentally found within the blood vessel of a normal tissue portion of a human lung cancer resected specimen) immunohisto-chemically stained with humanized 1101 antibody and humanized 99 antibody.

Figure 5:
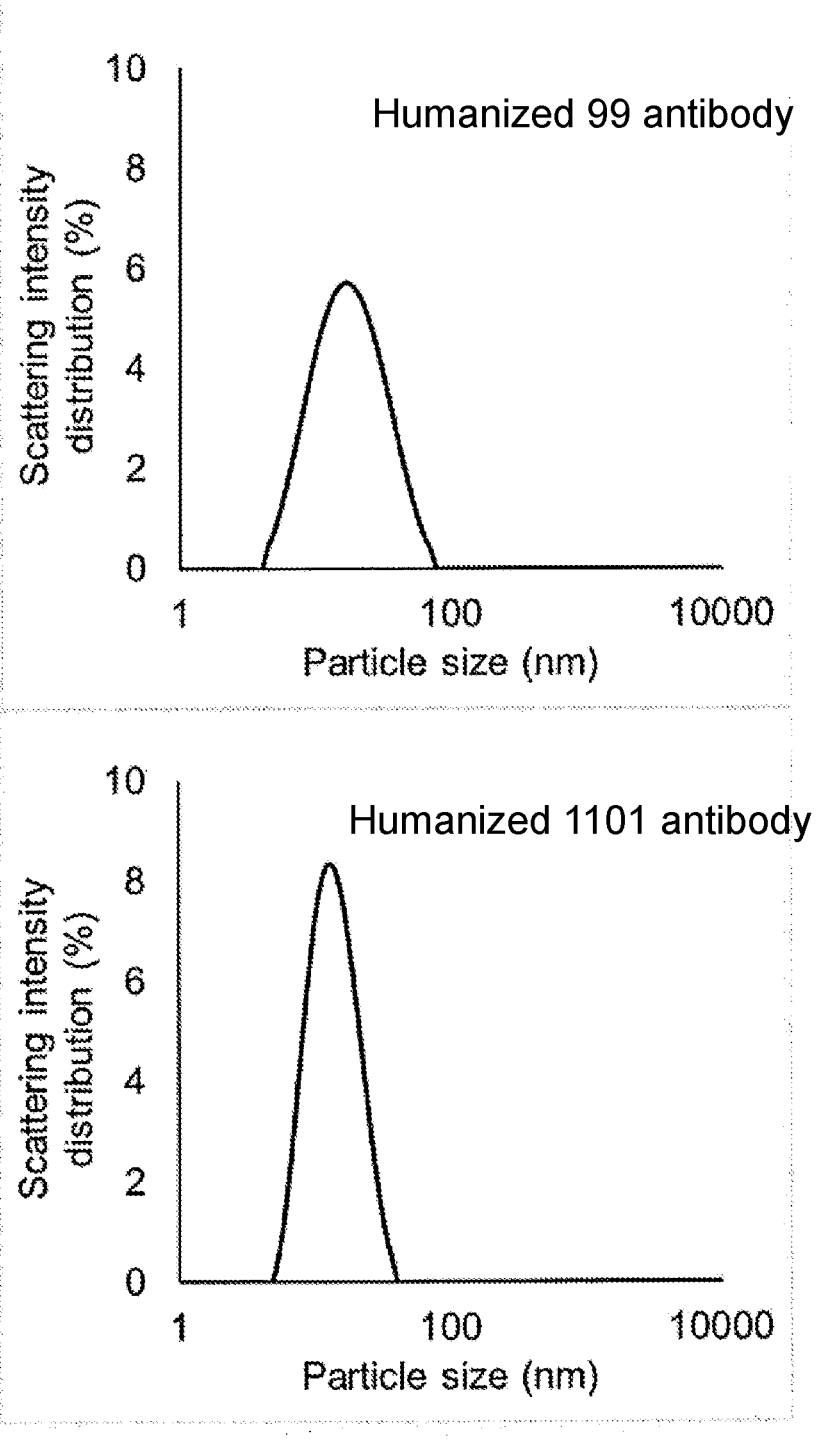

FIG. 5 shows the results of measurement of particle sizes (nm) of humanized 99 antibody and humanized 1101 anti-body expressed in Chinese hamster ovary cells (CHO cell), by DelsaNano (trademark).

DETAILED DESCRIPTION OF THE INVENTION

As used herein, the term "subject" is a mammal. The mammal can be a dog, a cat, a cow, a horse, a pig, a primate (for example, a monkey, a gorilla, an orangutan, a bonobo, a chimpanzee and a human), and more specifically, a human.

As used herein, the term "treatment" means to include therapy (therapeutic treatment) and prevention (prophylactic treatment). As used herein, the "therapy" means treating, curing and inhibiting a disease or disorder, achieving a remission or delaying progression of a disease or disorder. As used herein, "prevention" means decreasing the possi-bility of developing a disease or pathological condition, or delaying developing a disease or a pathological condition.

As used herein, the term "disease" refers to a symptom on which a treatment has a beneficial effect. As used herein, the term "cancer" refers to a malignant tumor.

As used herein, the term "therapeutically effective amount" refers to an effective amount of a medicinal agent for treating (preventing or therapeutically treating) a disease and a condition. A therapeutically effective amount of a medicinal agent enables to delay worsening a disease or condition, stop symptomatic worsening, produce symptom-atic improvement, cure the symptom or suppress onset or development of the symptom.

As used herein, the term "fibrin" refers to an insoluble coagulate formed by cleaving the C terminal of three types of polypeptide chains (Aα chain, Bβ chain and γ chain) that form fibrinogen. In the specification, fibrin will be some-times referred to as insoluble fibrin. More specifically, when the C terminal of fibrinogen is cleaved, fibrinogen is con-verted into the state called a fibrin monomer. The fibrin monomers are polymerized by the action of calcium to form a poor-soluble fibrin polymer. The fibrin polymers are crosslinked between the polymers by the action of factor XIII to form stable fibrin (insoluble fibrin defined in the specification or fibrin gel). Insoluble fibrin is decomposed by plasmin. Plasmin is contained in the plasma in the form of a precursor, plasminogen. When plasminogen is decom-posed with, e.g., a plasminogen activator (for example, urokinase, tissue plasminogen activator and streptokinase), more specifically, when the peptide between Arg and Val of plasminogen is decomposed, plasmin is produced. Plasmin is inhibited by a protein called a plasmin inhibitor and can be limited in action.

Aα chain of fibrinogen may be Aα chain of human fibrinogen. Examples of Aα chain of human fibrinogen include Aα chain of human fibrinogen having the amino acid sequence registered under GenBank registration number: AA101936.1, and Aα chain of human fibrinogen having an amino acid sequence corresponding to the amino acid sequence.

Bβ chain of fibrinogen may be Bβ chain of human fibrinogen. Examples of Bβ chain of human fibrinogen include β chain of human fibrinogen having the amino acid sequence registered under NCBI reference number: NP_005132.2, and β chain of human fibrinogen having an amino acid sequence corresponding to the amino acid sequence.

γ chain of fibrinogen may be γ chain of human fibrinogen. Examples of γ chain of human fibrinogen include γ chain of human fibrinogen having the amino acid sequence registered under GenBank registration number: AAH07044.1, and γ chain of human fibrinogen having an amino acid sequence corresponding to the amino acid sequence.

As used herein, the term "antibody" refers to an immu-noglobulin. The antibody may be one of the isotypes, for example, IgG. The antibody may be preferably a monoclo-nal antibody. The antibody may be a human chimeric antibody, a humanized antibody or a human antibody. The human chimeric antibody may be prepared by replacing a constant region of a non-human antibody with that of a human antibody. A humanized antibody may be prepared by replacing 6 CDRs of a human antibody with the correspond-ing 6 CDRs of a non-human antibody. A human antibody may be prepared by use of an animal (for example, mouse) in which at least a heavy chain variable region of an immunoglobulin is replaced with the corresponding region of a human locus. If the constant region is derived from a non-human animal, the constant region is replaced with the amino acid sequence of a human antibody. In this manner, a human antibody can be obtained. In the specification, the antibody may be preferably a humanized antibody. In the specification, the antibody may be preferably a human antibody. An antibody produced in a cell has a signal peptide but the signal peptide is cut out when it is released from the cell. Thus, when an antibody is administered as a medical agent, a signal peptide of the antibody is not required.

As used herein, the term "CDR" refers to a complemen-tarity determining region present in a heavy chain variable region and a light chain variable region of an antibody. Three CDRs are present in each of the heavy chain and light chain variable regions and called as CDR1, CDR2 and CDR3 in the order from the N terminal. CDRs can be determined based on, for example, the numbering scheme by Kabat et. al (Kabat, E. A. et al., Sequences of Proteins of Immuno-logical Interest, 5th ed., 1991, Bethesda: US Dept. of Health and Human Services, PHS, NIH).

As used herein, the term "insoluble fibrin-specific anti-body" refers to an antibody that binds to insoluble fibrin and having a stronger affinity to insoluble fibrin than to fibrino-gen. The insoluble fibrin-specific antibody can be easily obtained by screening based on affinity to an insoluble fibrin and affinity to fibrinogen. Fibrin has an epitope site, which is exposed for the first time when a conformational change occurs in fibrin and fibrin changes insoluble fibrin. Therefore, the "insoluble fibrin-specific antibody" can be obtained by immunization using the exposed site (domain), in other words, D domain (hereinafter referred to also as "D-domain") as an immunogen. Alternatively, the "insoluble fibrin-specific antibody" can be obtained by a linear peptide. For example, the immunization with a partial peptide of the fibrin Bβ chain corresponding to 231 to 246 positions of the amino acid sequence of fibrin Bβ chain (for example, human fibrin Bβ chain can have the amino acid sequence set forth in SEQ ID NO:17) can provide the "insoluble fibrin-specific antibody". Other than this, the "insoluble fibrin-specific antibody" can be obtained by immunization with a peptide consisting of the amino acid sequence set forth in SEQ ID NO:18 used as an immunogen. Such an insoluble fibrin-specific antibody can be an antibody having a stronger affinity to insoluble fibrin than to any one of fibrinogen, a fibrin monomer and a fibrin polymer. If the ratio of affinity of an antibody to insoluble fibrin and affinity thereof to fibrinogen is, for example, beyond 1 (e.g., 1.5 or more, 2 or more, 3 or more, 4 or more, or 5 or more), the antibody can be an insoluble fibrin-specific antibody. The affinity refers to binding affinity (KD), which can be determined by a method commonly known in the technical field such as ELISA and Kinetic Exclusion Assay. As used herein, strong affinity means that KD is low. As used herein, weak affinity means that KD is high.

As used herein, the term "compete" means that an antibody competes with another antibody for binding to an antigen. Competitive binding occurs in the case where two antibodies bind to the same binding site of an antigen. Such an antibody can be obtained by immunization using an epitope as mentioned above and/or confirmed by a competition binding assay, more specifically, checking whether the binding of an antibody to an antigen is reduced or not by the presence of the other antibody. Competitive antibodies include antibodies competing with each other.

As used herein, the term "antibody-drug conjugate" (hereinafter referred to also as "ADC") refers to a substance prepared by connecting an antibody and a cytotoxic agent to each other. In ADC, an antibody and a cytotoxic agent can be linked via an appropriate linker. Examples of the cytotoxic agent that can be used herein include a chemotherapeutic agent, a radioisotope and a toxin. A conjugate composed of an antigen-binding fragment of an antibody and a drug may be included in ADC.

As used herein, the term "antigen-binding fragment of an antibody" refers to an antibody fragment having a binding ability to an antigen. Examples of the antigen-binding fragment include Fab, Fab', F(ab')$_2$, Fv, scFv (single chain Fv), diabody and sc(Fv)$_2$ (single chain (Fv)$_2$). For example, Fab can be obtained by digesting an antibody with papain. F(ab')$_2$ can be obtained by digesting an antibody with pepsin. If F(ab')$_2$ is further reduced, Fab' can be obtained. Other antigen-binding fragments of an antibody can be prepared by methods commonly known to those skilled in the art. In the present invention, the antigen-binding fragments of an antibody as mentioned above can be used.

In the present invention, an antibody that binds to insoluble fibrin is an antibody that binds to insoluble fibrin with a stronger affinity than to fibrinogen (in other words, an antibody that binds to insoluble fibrin with low dissociation constant KD than to fibrinogen). The antibody that binds to insoluble fibrin with a stronger affinity than to fibrinogen can be, for example, an antibody that binds to a peptide consisting of the amino acid sequence set forth in SEQ ID NO:17 or 18 (see WO2014/133093). The amino acid sequence set forth in SEQ ID NO:17 corresponds to the amino acid sequence set forth in SEQ ID NO:1 in WO2014/133093. The amino acid sequence set forth in SEQ ID NO:18 corresponds to the amino acid sequence set forth in SEQ ID NO:2 in WO2014/133093.

The antibody that binds to insoluble fibrin with a stronger affinity than to fibrinogen or an antigen-binding fragment thereof is, for example, an antibody or an antigen-binding fragment thereof having CDRs corresponding to heavy chain CDR1 to 3 and light chain CDR1 to 3 of an antibody selected from the group consisting of 10-102 antibody, 34-105 antibody and Fib-0355 antibody disclosed in WO2014/133093.

The antibody that binds to insoluble fibrin with a stronger affinity than to fibrinogen or an antigen-binding fragment thereof is, for example, an antibody or an antigen-binding fragment thereof having CDRs corresponding to heavy chain CDR1 to 3 and light chain CDR1 to 3 of an antibody selected from the group consisting of 99 antibody, 1101 antibody and 0211 antibody disclosed in WO2018/203517.

The antibody that binds to insoluble fibrin with a stronger affinity than to fibrinogen or an antigen-binding fragment thereof is, for example, an antibody or an antigen-binding fragment thereof containing a heavy chain variable region containing heavy chain CDR1 having the amino acid sequence set forth in SEQ ID NO:1, heavy chain CDR2 having the amino acid sequence set forth in SEQ ID NO:2 and heavy chain CDR3 having the amino acid sequence set forth in SEQ ID NO:3, and a light chain variable region containing light chain CDR1 having the amino acid sequence set forth in SEQ ID NO:4, light chain CDR2 having the amino acid sequence set forth in SEQ ID NO:5 and light chain CDR3 having the amino acid sequence set forth in SEQ ID NO:6.

The antibody can be a human chimeric antibody or a humanized antibody. According to the present invention, there is also provided a humanized antibody having the heavy chain variable region and the light chain variable region mentioned above.

The antibody that binds to insoluble fibrin with a stronger affinity than to fibrinogen or an antigen-binding fragment thereof is, for example, an antibody or an antigen-binding fragment thereof having a heavy chain variable region having the amino acid sequence set forth in SEQ ID NO:7 and a light chain variable region set forth in SEQ ID NO:8. The antibody may further contain a heavy chain constant region within Fab fragment or a part thereof in addition to the heavy chain variable region. The antibody can be a human chimeric antibody or a humanized antibody. According to the present invention, there is also provided a humanized antibody having the heavy chain variable region and the light chain variable region mentioned above.

The antibody that binds to insoluble fibrin with a stronger affinity than to fibrinogen or an antigen-binding fragment thereof is, for example, an antibody or an antigen-binding fragment thereof containing a heavy chain variable region containing heavy chain CDR1 having the amino acid sequence set forth in SEQ ID NO:9, heavy chain CDR2 having the amino acid sequence set forth in SEQ ID NO:10 and heavy chain CDR3 having the amino acid sequence set forth in SEQ ID NO:11, and a light chain variable region containing light chain CDR1 having the amino acid sequence set forth in SEQ ID NO:12, light chain CDR2 having the amino acid sequence set forth in SEQ ID NO:13 and Light chain CDR3 having the amino acid sequence set forth in SEQ ID NO:14.

The antibody can be a human chimeric antibody or a humanized antibody. According to the present invention, there is also provided a humanized antibody having the heavy chain variable region and the light chain variable region mentioned above.

The antibody that binds to insoluble fibrin with a stronger affinity than to fibrinogen or an antigen-binding fragment thereof is, for example, an antibody or an antigen-binding fragment thereof containing a heavy chain variable region having the amino acid sequence set forth in SEQ ID NO:15, and light chain variable region having the amino acid sequence set forth in SEQ ID NO:16.

The antibody may further contain heavy chain constant region in Fab fragment or a part thereof in addition to the heavy chain variable region. The antibody can be a human chimeric antibody or a humanized antibody. According to the present invention, there is also provided a humanized antibody having the heavy chain variable region and the light chain variable region mentioned above.

According to the present invention, there can be provided an antibody which competes with the antibody described in the above (3), preferably an antibody which competes with the antibody mutually, for binding to insoluble fibrin. The antibody herein is preferably a humanized antibody.

According to the present invention, there can be provided an antibody which competes with the antibody described in the above (4), preferably an antibody which competes with the antibody mutually, for binding to insoluble fibrin. The antibody herein is preferably a humanized antibody.

According to the present invention, the antibody described in the above (1) can be a humanized antibody and an insoluble fibrin-specific antibody.

According to the present invention, the antibody described in the above (2) can be a humanized antibody and an insoluble fibrin-specific antibody.

According to the present invention, the antibody described in the above (3) can be a humanized antibody and an insoluble fibrin-specific antibody.

According to the present invention, the antibody described in the above (4) can be a humanized antibody and an insoluble fibrin-specific antibody.

According to the present invention, an antibody which competes with the antibody described in the above (3), preferably an antibody which competes with the antibody mutually, for binding to insoluble fibrin is a humanized antibody and an insoluble fibrin-specific antibody.

According to the present invention, an antibody which competes with the antibody described in the above (4), preferably an antibody which competes with the antibody mutually, for binding to insoluble fibrin is a humanized antibody and an insoluble fibrin-specific antibody.

The antibody of the present invention can bind to a peptide consisting of the amino acid sequence set forth in SEQ ID NO:17. The antibody of the present invention herein can be a humanized antibody. The antibody of the present invention is a humanized antibody that can bind to the peptide consisting of the amino acid sequence set forth in SEQ ID NO:17 and selected from the aforementioned antibodies. The antibody of the present invention can be a humanized antibody that can bind to the peptide consisting of the amino acid sequence set forth in SEQ ID NO:17 and has an amino acid identity of 90% or more, 91% or more, 92% or more, 93% or more, 94% or more, or 95% or more to the above antibody in a heavy chain or light chain variable region. The antibody of the present invention can be a humanized antibody that can bind to the peptide consisting of the amino acid sequence set forth in SEQ ID NO:17 and may have an insert, deletion, replacement or addition of a single amino acid in heavy chain or light chain variable region of the above antibody. The antibody of the present invention can be a humanized antibody that can bind to the peptide consisting of the amino acid sequence set forth in SEQ ID NO:17 and may have an insert, deletion, replacement or addition of two amino acids in heavy chain or light chain variable region of the above antibody.

The antibody of the present invention can be used as the antibody (portion) in an antibody-drug conjugate.

In the antibody-drug conjugate of the present invention, the antibody and a cytotoxic agent (drug) are connected via a linker. Examples of the cytotoxic agent include chemotherapeutic agents (for example, an anti-cancer agent such as a commercially available anti-cancer agent including auristatin (auristatin E, auristatin F phenylenediamine (AFP), monomethyl auristatin E, monomethyl auristatin F and a derivative thereof), maytansinoid DM1 and DM4 and derivatives thereof, camptothecins (SN-38, irinotecan, lurtotecan, DB67, BMP1350, ST1481, CKD602, topotecan and exatecan, and derivatives thereof), DNA minor groove binders (enediyne, lexitropsin, duocarmycin and derivatives thereof), taxanes (paclitaxel, docetaxel and derivatives thereof), polyketides (discodermolide and a derivative thereof), anthraquinones (mitoxantrone and a derivative thereof), benzodiazepines (pyrrolobenzodiazepines, indolinobenzodiazepine, oxazolidinobenzodiazepine and derivatives thereof), vinca alkaloids (vincristine, vinblastine, vindesine, vinorelbine and derivatives thereof), doxorubicins (doxorubicin, morpholine-doxorubicin, cyanomorpholino-doxorubicin and derivatives thereof), cardiac glycosides (digitoxin and a derivative thereof), calicheamicin, epothilone, cryptophycin, semadotin, semadotin, rhizoxin, netropsin, combretastatin, eleutherobin, etoposide, T67 (Tularik), and nocodazole), radioisotopes (for example, $^{32}$P, $^{60}$C, $^{90}$Y, $^{111}$In, $^{131}$I, $^{125}$I, $^{153}$Sm, $^{186}$Re, $^{188}$Re, and $^{212}$Bi), and toxins (for example, diphtheria toxin A, pseudomonas endotoxin, ricin, saporin), which can be used as the cytotoxic agent of ADC of the present invention. As the cytotoxic agent of ADC of the present invention, preferably, for example, camptothecin, particularly SN-38, or exatecan, can be used. As the cytotoxic agent, an agent for treating a cancer can be used. The cytotoxic agent to be used may be a pharmaceutically acceptable salt, solvate (for example, hydrate), ester or prodrug of a cytotoxic agent as mentioned above.

In ADC of the present invention, an antibody and a cytotoxic agent may be connected via a linker. In the present invention, the linker may be a non-cleavable linker or a cleavage linker. Linkers different in structure are known to be used in ordinary ADC and they can be appropriately used herein.

In an embodiment of the present invention, the linker of ADC contains a plasmin cleavage sequence and can be cleaved in the presence of plasmin. In the present invention, the site (sequence) except the plasmin cleavage sequence of the linker for ADC has a stable chemical bond until the ADC is delivered (exposed) to insoluble fibrin after administration. Due to the structure, ADC of the present invention is kept stable until it is delivered (exposed) to insoluble fibrin after administration, and then, after ADC binds to insoluble fibrin, it is cleaved with plasmin and releases a cytotoxic agent only in the vicinity of insoluble fibrin. The plasmin cleavage sequence consists of an amino acid sequence, and more specifically, is a peptide chain containing an amino acid sequence selected from the group consisting of valineleucine-lysine, glycine-proline-lysine, glutamic acid-lysine-lysine, lysine-phenylalanine-lysine, norvaline-chlorohexyl-alanyl-lysine, and norleucine-hexahydrotyrosine-lysine. Such a linker can be appropriately selected and synthesized by those skilled in the art in a process for preparing ADC. In an embodiment, the linker may have a spacer (first spacer), which is introduced between an antibody and a plasmin cleavage sequence. As the first spacer, for example, polyethylene glycol (PEG), for example, PEG having about 5 to 40 repeat units per molecule, can be used. A second spacer may be introduced between the plasmin cleavage sequence and a cytotoxic agent. As the second spacer, for example, p-aminobenzyloxycarbonyl (PABC) can be used.

In an embodiment, the linker contains a first spacer and a plasmin cleavage sequence. In an embodiment, the linker contains a first spacer, a plasmin cleavage sequence and a second spacer. In a predetermined subject (embodiment), the linker contains PEG, a plasmin cleavage sequence and PABC.

In an embodiment, the linker does not contain a cleavage part (sequence) except a plasmin cleavage sequence.

In linking an antibody and a linker, the antibody is linked via its sulfhydryl group to the linker with a maleimide group interposed between them.

In an embodiment, an antibody is linked via its sulfhydryl group to an anti-cancer agent with a linker having maleimide-PEG-plasmin cleavage sequence interposed between them. In an embodiment, an antibody is linked via its sulfhydryl group to an anti-cancer agent by a linker having maleimide-PEG-plasmin cleavage sequence-PABC.

In any case, in ADC of the present invention, an anti-cancer agent is linked to an anti-cancer agent with a linker having a plasmin cleavage site (cleavable with plasmin). When ADC reaches a site where insoluble fibrin is accumulated, the linker is cleaved at a plasmin cleavable site by plasmin present therearound. In this way, an anti-cancer agent is released around insoluble fibrin. It is considered that there are many sites having insoluble fibrin accumulated around a cancer tissue based on bleeding caused by infiltration of cancer (see, WO2018/203517, FIG. 8). Because of this, it is considered that the antibody of the present invention (more specifically, insoluble fibrin-specific antibody) is useful for a drug delivery system targeting cancer, and that ADC of the present invention is useful as a therapeutic drug for cancer.

Examples of the target cancer to be treated by ADC or a pharmaceutical composition of the present invention include, but are not particularly limited to, cancers such as lung cancer, pancreatic cancer, head and neck cancer, prostate cancer, bladder cancer, breast cancer, esophageal cancer, gastric cancer, colorectal cancer, uterine cancer, ovarian cancer, skin cancer, thyroid cancer, thymus cancer, kidney cancer, testicular cancer, penile cancer, liver cancer, biliary tract cancer, brain tumor, bone and soft tissue tumor, retroperitoneal tumor, angiosarcoma, and lymphangiosarcoma, and these metastatic cancers.

Examples of the subject of the present invention may include a subject not having a thrombotic disorder or a disease associated with a thrombotic disorder and a subject not yet diagnosed as a thrombotic disorder or a disease associated with a thrombotic disorder. Due to this, it can be expected to reduce a side effect in tissues except a cancer tissue. Thus, subjects having a cancer are first determined as to whether they have a thrombotic disorder or a disease associated with a thrombotic disorder, and then, administration of ADC of the present invention is allowed to subjects not having a thrombotic disorder or a disease associated with a thrombotic disorder. Whether or not a subject has a thrombotic disorder or a disease associated with a thrombotic disorder can be appropriately determined by a doctor.

In an embodiment of the present invention, a pharmaceutical composition contains ADC of the present invention and an excipient. The pharmaceutical composition of the present invention can be, e.g., intravenously, subcutaneously, intra-tumorally, intraperitoneally, intracerebroventricularly or intramuscularly administered. The dose of the composition can be appropriately determined by a doctor in consideration of, e.g., the age, sex, body weight and severity of a disease of the patient.

ADC of the present invention is targeted to insoluble fibrin accumulated in the interstitium of a cancer as mentioned above and accumulates a cytotoxic agent at the targeted site. Other than this, ADC of the present invention has a linker cleavable with plasmin, which is activated in the presence of insoluble fibrin and releases the cytotoxic agent at the target site. In this way, ADC can damage a cancer around the release site in a site-specific manner.

According to the present invention, there is provided use of an insoluble fibrin-specific antibody in manufacture of a medicament for use in treating a cancer. According to the present invention, there is provided use of an ADC comprising an insoluble fibrin-specific antibody and a cytotoxic agent in manufacture of a medicament for use in treating a cancer, and more specifically, use of an ADC comprising the antibody and a cytotoxic agent having a plasmin cleavable site (that can be cleaved with plasmin).

According to the present invention, there is provided a method for treating a cancer in a subject in need thereof, including administering a therapeutically effective amount of ADC of the present invention to the subject. According to the present invention, there is provided a method for treating a cancer in a subject in need thereof, including determining whether or not a subject having a cancer is affected with a thrombotic disorder or a disease associated with a thrombotic disorder, and then, administering a therapeutically effective amount of ADC of the present invention only to a subject not affected with a thrombotic disorder or a disease associated with a thrombotic disorder.

According to the present invention, there is provided use of ADC of the present invention in a method for treating a cancer.

According to the present invention, the antibody of the present invention can be prepared by a method known to those skilled in the art. For example, the antibody of the present invention can be expressed in cells (insect cells, bird cells, *Escherichia coli* cells, yeast cells, and mammalian cells), preferably, mammalian cells (for example, cells suitable for expressing a protein, for example, Chinese hamster ovary cells (CHO cells) and mammalian cells suitable for expressing a protein, such as 293 cells and cells derived from these). Expression can be made by using an expression vector, which contains a nucleic acid encoding a fusion protein of the present invention and is operably linked to a promoter operational in the expression cells mentioned above. If a fusion protein must contain a light chain, the light chain can be co-expressed by the expression cells. According to the present invention, the fusion protein of the present invention can be purified by a purification method known to those skilled in the art. Purification can be carried out by, e.g., an affinity column containing an antigen or an affinity column to a tag attached to a fusion protein.

According to the present invention, there is provided a composition and pharmaceutical composition containing the antibody of the present invention or an antigen-binding fragment thereof. The pharmaceutical composition of the present invention may contain the antibody of the present invention or an antigen-binding fragment thereof and further a pharmaceutically acceptable excipient. Examples of the pharmaceutically acceptable excipient include a salt, a tonicity agent, a pH regulator and water. In an embodiment, the pharmaceutical composition of the present invention can be provided in the form of a kit containing a lyophilized pharmaceutical composition and water for injection (i.e., a kit for preparing an injection just before use).

A pharmaceutical composition containing the antibody of the present invention or an antigen-binding fragment thereof can be parenterally administered (for example, intravenous administration). Also, when the pharmaceutical composition of the present invention is intravenously administered, the pharmaceutical composition can be prepared so as to be suitable for intravenous administration. The pharmaceutical composition for intravenous administration can be appropriately prepared by those skilled in the art in the same manner as preparation of, for example, a protein preparation and an antibody preparation. The dose, administration timing, route of administration and others can be appropriately determined by a doctor.

In the pharmaceutical composition of the present invention, an antibody or an antigen-binding fragment thereof can be contained in a therapeutically effective amount.

In an embodiment of the present invention, an antibody can be linked to a detectable label for in-vivo imaging. The detectable label includes (is) an isotope selected from the group consisting of $^{177}$Lu, $^{111}$indium, $^{67}$Cu, $^{18}$F, $^{99m}$Tc, $^{124}$I, $^{125}$I and $^{131}$I. The detectable label may be a radioactive substance for positron emission tomography (PET). Examples of the radioactive substance include, but are not limited to, $^{124}$I and $^{89}$Zr. In a predetermined embodiment, the first and/or second antibody or an antigen binding portion or derivative thereof is tagged with a radioactive label. The radioactive label may be at least one of $^{177}$Lu, $^{111}$indium, $^{67}$Cu, $^{18}$F, $^{99m}$Tc, $^{124}$I, $^{125}$I, $^{131}$I and $^{99m}$Tc.

The detectable label is not limited as long as it is suitable for in-vitro and/or in-vivo imaging. The imaging may include at least one of planar radionuclide imaging, positron emission tomography (PET), echo plane imaging (EPI), single photon emission computer tomography (SPECT), ultrasound imaging (e.g., non-radioactive, contrast specific, high frequency, two dimension), magnetic resonance imaging (MRI, also called as magnetic resonance tomography or MRT), X-ray or computer tomography (CT) scan, fluorescence imaging, near infrared imaging, and other imaging methods useful for or applicable to medical use. Accordingly, a contrast medium or imaging agent suitable for each of these imaging methods can be linked to an antibody.

According to the present invention, there is provided an antibody (of the present invention) linked to a detectable label for in-vivo imaging and a diagnostic agent or diagnostic kit containing the antibody.

According to the present invention, there is provided a method for observing in-vivo fibrin in a subject, including administering, to a subject, an effective amount of the antibody of the present invention tagged with a detectable label for in-vivo imaging.

EXAMPLES

Example 1: Preparation of Humanized 1101 Antibody and Humanized 99 Antibody

An antibody (1101 antibody) produced by 1101 clone and a monoclonal antibody (99 antibody) produced by 99 clone disclosed in WO2018/203517 were humanized to obtain humanized 1101 antibody and humanized 99 antibody, respectively. In a humanization process, the sequence of CDR was modified to improve binding affinity to insoluble fibrin.

Figure 1:
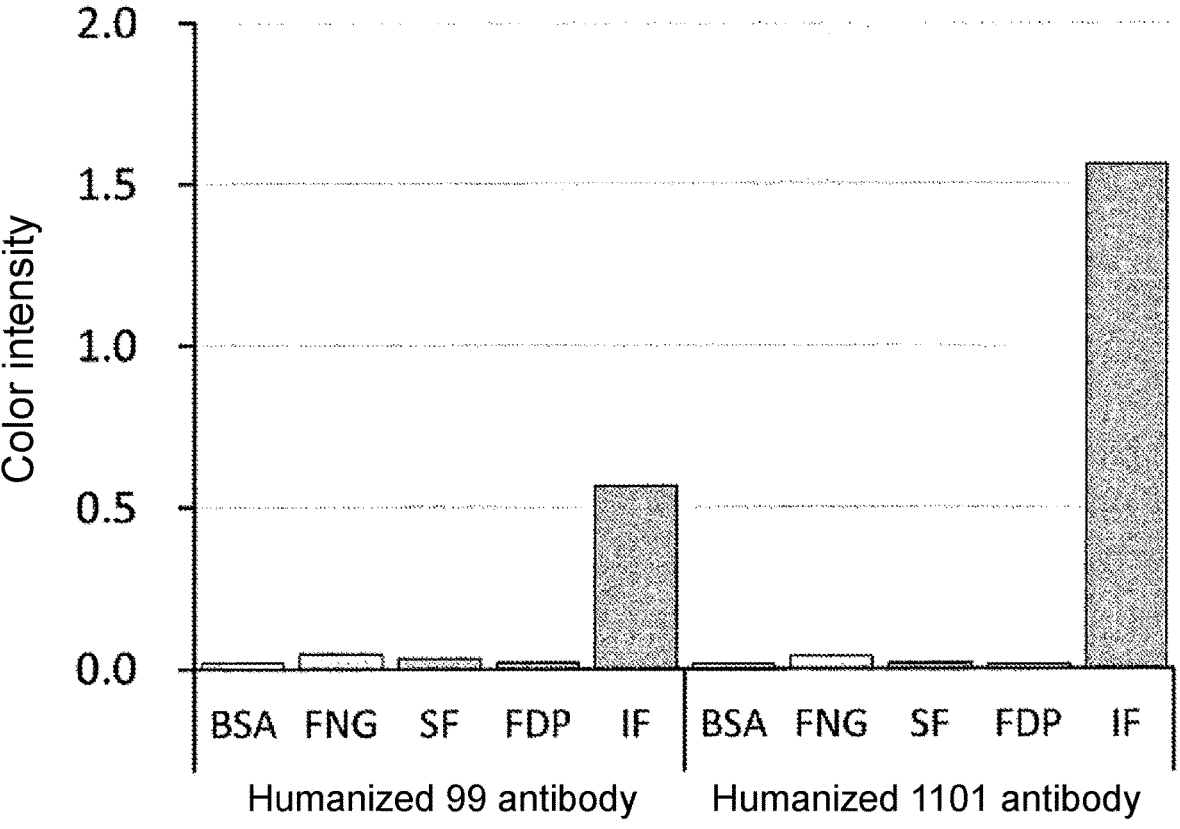
FIG. 1 shows the ELISA assay results showing binding abilities of humanized 99 antibody and humanized 1101 antibody to antigens. BSA represents bovine serum albumin; FNG fibrinogen, SF soluble fibrin, FDP fibrin degradation product and IF insoluble fibrin.

The binding ability of each of the humanized 1101 antibody and humanized 99 antibody obtained to insoluble fibrin was checked by ELISA assay. ELISA (plates) were prepared by coating plates separately with bovine serum albumin (BSA), fibrinogen (FNG), soluble fibrin (SF), a fibrin degradation product (FDP) and insoluble fibrin (IF). The surface of ELISA plates was blocked with TBS-T containing 1% BSA and 0.05% Tween20, and then, HRP-labeled humanized 1101 antibody and HRP-labeled humanized 99 antibody were added and allowed to react. Then, the substrate for HRP, i.e., TMB reagent, was added to develop a color, which was detected by a microplate reader (SpectraMax Paradigm, Molecular Device). The color-intensity results were as shown in FIG. 1. As is apparent from FIG. 1, humanized 99 antibody and humanized 1101 antibody specifically bound to insoluble fibrin.

Subsequently, the binding ability of each of humanized 1101 antibody and humanized 99 antibody to denatured fibrinogen was checked by western blotting. A fibrinogen solution was diluted with a loading buffer containing 2-mercaptoethanol and SDS, and heated at 95° C. to obtain denatured fibrinogen. The denatured fibrinogen thus obtained was subjected to SDS-PAGE, transferred to a PVDF membrane and blocked with StartingBlock™ (TBS) Blocking Buffer (Thermo Fisher). Thereafter, humanized 1101 antibody and humanized 99 antibody were allowed to react with the membrane. Similarly to insoluble fibrin, the denatured fibrinogen exposes a site (which is specifically exposed in insoluble fibrin) to which humanized 1101 antibody and humanized 99 antibody are to be bound, humanized 1101 antibody and humanized 99 antibody can bind to the site. After the membrane was washed and blocked, western blotting was carried out using a HRP labeled anti-human IgG antibody (Bethyl) as a secondary antibody, and ECL (trademark) Prime Western Blotting Detection Reagent (Thermo Fisher) as a luminescent reagent. Imaging and image analysis were carried out by ChemiDoc imaging system (Bio-rad). As a result, as shown in FIG. 2, denatured fibrin was detected by humanized 1101 antibody and humanized 99 antibody both at a concentration of 0.04 µ/mL.

Immunohistochemical staining (IHC staining) was further carried out by humanized 1101 antibody and humanized 99 antibody. Slices of the pancreatic tissue taken from a pancreatic cancer model mouse (HE-PKC mouse) were fixed with paraformaldehyde in accordance with a customary method to prepare tissue sections. After blocking was carried out with PBS containing 1% BSA, humanized 1101 antibody and humanized 99 antibody (10 mg or 1 mg) were allowed to react with the obtained tissue sections. The sections were stained with a secondary antibody, i.e., Alexa 647 labeled anti-human IgG (Jackson Immunotechnology) and a nuclear staining reagent, i.e., DAPI. Imaging of the sections was carried out by Virtual Slide (Olympus Life Science), and image analysis was carried out by OlyVIA. The results were as shown in FIG. 3. As is apparent from FIG. 3, it was found that the humanized 1101 antibody and humanized 99 antibody thus obtained are useful for IHC staining.

In the blood vessel of the normal tissue of human lung cancer resected specimen, we found a site in which blood clot is present. The blood clot was immunohistochemically stained with humanized 1101 antibody and humanized 99 antibody in the same manner as above. The results were as shown in FIG. 4. As is apparent from FIG. 4, blood clot was successfully visualized by each of humanized 1101 antibody and humanized 99 antibody. In other words, humanized 1101 antibody and humanized 99 antibody were found to bind to human blood clot.

Subsequently, recombinant CHO cells expressing humanized 99 antibody and humanized 1101 antibody were prepared. The particle size (nm) of humanized 1101 antibody and humanized 99 antibody produced was measured by Delsa (trademark) Nano HC (Beckman Coulter). The results were as shown in FIG. 5. As is apparent form FIG. 5, it was found that the particle size of each of humanized 1101 antibody and humanized 99 antibody exhibits a monodisperse distribution, and that humanized 1101 antibody is more uniform in particle size.

Sequence Listing

SEQ ID NO:1: Amino acid sequence of heavy chain CDR1 of humanized anti-fibrin antibody 1101 clone SEQ ID NO:2: Amino acid sequence of heavy chain CDR2 of humanized anti-fibrin antibody 1101 clone SEQ ID NO:3: Amino acid sequence of heavy chain CDR3 of humanized anti-fibrin antibody 1101 clone SEQ ID NO:4: Amino acid sequence of light chain CDR1 of humanized anti-fibrin antibody 1101 clone SEQ ID NO:5: Amino acid sequence of light chain CDR2 of humanized anti-fibrin antibody 1101 clone SEQ ID NO:6: Amino acid sequence of light chain CDR3 of humanized anti-fibrin antibody 1101 clone SEQ ID NO:7: Amino acid sequence of heavy chain variable region of anti-fibrin antibody 1101 clone SEQ ID NO:8: Amino acid sequence of light chain variable region of anti-fibrin antibody 1101 clone SEQ ID NO:9: Amino acid sequence of heavy chain CDR1 of humanized anti-fibrin antibody 99 clone SEQ ID NO:10: Amino acid sequence of heavy chain CDR2 of humanized anti-fibrin antibody 99 clone SEQ ID NO:11: Amino acid sequence of heavy chain CDR3 of humanized anti-fibrin antibody 99 clone SEQ ID NO:12: Amino acid sequence of light chain CDR1 of humanized anti-fibrin antibody 99 clone SEQ ID NO:13: Amino acid sequence of light chain CDR2 of humanized anti-fibrin antibody 99 clone SEQ ID NO:14: Amino acid sequence of light chain CDR3 of humanized anti-fibrin antibody 99 clone SEQ ID NO:15: Amino acid sequence of heavy chain variable region of humanized anti-fibrin antibody 99 clone SEQ ID NO:16: Amino acid sequence of light chain variable region of humanized anti-fibrin antibody 99 clone SEQ ID NO:17: part of amino acid sequence exposed in insoluble fibrin (β chain)

SEQ ID NO:18: part of amino acid sequence exposed in insoluble fibrin (γ chain)

---

The invention claimed is:

1. An antibody that binds to insoluble fibrin or an antigen-binding fragment thereof, comprising (1) a heavy chain variable region comprising heavy chain CDR1 having an amino acid sequence set forth in SEQ ID NO:1, heavy chain CDR2 having an amino acid sequence set forth in SEQ ID NO:2 and heavy chain CDR3 having an amino acid sequence set forth in SEQ ID NO:3, and a light chain variable region comprising light chain CDR1 having an amino acid sequence set forth in SEQ ID NO:4, light chain CDR2 having an amino acid sequence set forth in SEQ ID NO:5 and Light chain CDR3 having an amino acid sequence set forth in SEQ ID NO:6; or (2) a heavy chain variable region comprising heavy chain CDR1 having an amino acid sequence set forth in SEQ ID NO:9, heavy chain CDR2 having an amino acid sequence set forth in SEQ ID NO:10 and heavy chain CDR3 having an amino acid sequence set forth in SEQ ID NO:11, and a light chain variable region comprising light chain CDR1 having an amino acid sequence set forth in SEQ ID NO:12, light chain CDR2 having an amino acid sequence set forth in SEQ ID NO:13 and light chain CDR3 having an amino acid sequence set forth in SEQ ID NO:14.

2. The antibody that binds to insoluble fibrin or an antigen-binding fragment thereof according to claim 1, comprising (3) a heavy chain variable region having an amino acid sequence set forth in SEQ ID NO:7 and a light chain variable region having an amino acid sequence set forth in SEQ ID NO:8; or (4) a heavy chain variable region having an amino acid sequence set forth in SEQ ID NO:15 and a light chain variable region having an amino acid sequence set forth in SEQ ID NO:16.

3. The antibody or an antigen-binding fragment thereof according to claim 1, which is a humanized antibody or an antigen-binding fragment thereof.

4. An antibody-drug conjugate comprising the antibody or an antigen-binding fragment thereof according to claim 1.

5. A pharmaceutical composition comprising the antibody-drug conjugate according to claim 4.

6. A method of treating cancer in a subject, the method comprising administering the pharmaceutical composition according to claim 5 to the subject.

7. An in-vivo diagnostic agent comprising the antibody or an antigen-binding fragment thereof according to claim 1.

* * * * *

SEQUENCE LISTING

```
<160> NUMBER OF SEQ ID NOS: 18

<210> SEQ ID NO 1
<211> LENGTH: 5
<212> TYPE: PRT
<213> ORGANISM: Artificial Sequence
<220> FEATURE:
<223> OTHER INFORMATION: HCDR1 of humanized 1101 clone

<400> SEQUENCE: 1

Ser Tyr Trp Met His
1               5

<210> SEQ ID NO 2
<211> LENGTH: 17
<212> TYPE: PRT
<213> ORGANISM: Artificial Sequence
<220> FEATURE:
<223> OTHER INFORMATION: HCDR2 of humanized 1101 clone

<400> SEQUENCE: 2

Ala Ile Tyr Pro Gly Asn Ser Asp Thr Arg Tyr Ser Pro Ser Phe Gln
1               5                   10                  15

Gly

<210> SEQ ID NO 3
<211> LENGTH: 11
<212> TYPE: PRT
<213> ORGANISM: Artificial Sequence
<220> FEATURE:
<223> OTHER INFORMATION: HCDR3 of humanized 1101 clone

<400> SEQUENCE: 3

Lys Ala His Tyr Gly Asn Tyr Gly Phe Ala Tyr
1               5                   10
```

```
<210> SEQ ID NO 4
<211> LENGTH: 11
<212> TYPE: PRT
<213> ORGANISM: Artificial Sequence
<220> FEATURE:
<223> OTHER INFORMATION: LCDR1 of humanized 1101 clone

<400> SEQUENCE: 4

Arg Ala Ser Gln His Ile Asn Asn Trp Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: LCDR2 of humanized 1101 clone

<400> SEQUENCE: 5

Gly Ala Thr Ser Leu Gln Ser
1               5

<210> SEQ ID NO 6
<211> LENGTH: 9
<212> TYPE: PRT
<213> ORGANISM: Artificial Sequence
<220> FEATURE:
<223> OTHER INFORMATION: LCDR3 of humanized 1101 clone

<400> SEQUENCE: 6

Gln Gln Tyr Trp Ser Thr Pro Leu Thr
1               5

<210> SEQ ID NO 7
<211> LENGTH: 242
<212> TYPE: PRT
<213> ORGANISM: Artificial Sequence
<220> FEATURE:
<223> OTHER INFORMATION: Fab region of heavy chain of humanized 1101
      clone

<400> SEQUENCE: 7

Met Gly Ser Thr Ala Ile Leu Ala Leu Leu Leu Ala Val Leu Gln Gly
1               5                   10                  15

Val Cys Ala Glu Val Gln Leu Val Gln Ser Gly Ala Glu Val Lys Lys
            20                  25                  30

Pro Gly Glu Ser Leu Lys Ile Ser Cys Lys Gly Ser Gly Tyr Ser Phe
        35                  40                  45

Thr Ser Tyr Trp Met His Trp Val Arg Gln Met Pro Gly Lys Gly Leu
    50                  55                  60

Glu Trp Ile Gly Ala Ile Tyr Pro Gly Asn Ser Asp Thr Arg Tyr Ser
65                  70                  75                  80

Pro Ser Phe Gln Gly Gln Val Thr Ile Ser Ala Asp Lys Ser Ile Ser
                85                  90                  95

Thr Ala Tyr Leu Gln Trp Ser Ser Leu Lys Ala Ser Asp Thr Ala Met
            100                 105                 110

Tyr Tyr Cys Thr Arg Lys Ala His Tyr Gly Asn Tyr Gly Phe Ala Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160
```

```
Thr Ala Ala Leu Gly Cys Leu Val Lys Asp Tyr Phe Pro Glu Pro Val
            165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
            195                 200                 205

Thr Val Pro Ser Ser Ser Leu Gly Thr Gln Thr Tyr Ile Cys Asn Val
            210                 215                 220

Asn His Lys Pro Ser Asn Thr Lys Val Asp Lys Lys Val Glu Pro Lys
225                 230                 235                 240

Ser Cys

<210> SEQ ID NO 8
<211> LENGTH: 236
<212> TYPE: PRT
<213> ORGANISM: Artificial Sequence
<220> FEATURE:
<223> OTHER INFORMATION: Light chain of humanized 1101 clone

<400> SEQUENCE: 8

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
            35                  40                  45

Gln His Ile Asn Asn Trp Leu Ala Trp Tyr Gln Gln Lys Pro Gly Lys
            50                  55                  60

Ala Pro Lys Leu Leu Ile Ser Gly Ala Thr Ser Leu Gln Ser Gly Val
65                  70                  75                  80

Pro Ser Arg Phe Ser Gly Ser Gly Ser Gly Thr Asp Phe Thr Leu Thr
            85                  90                  95

Ile Ser Ser Leu Gln Pro Glu Asp Phe Ala Thr Tyr Tyr Cys Gln Gln
            100                 105                 110

Tyr Trp Ser Thr Pro Leu Thr Phe Gly Gln Gly Thr Lys Val Glu Ile
            115                 120                 125

Lys Arg Thr Val Ala Ala Pro Ser Val Phe Ile Phe Pro Pro Ser Asp
            130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
            165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
            210                 215                 220

Ser Pro Val Thr Lys Ser Phe Asn Arg Gly Glu Cys
225                 230                 235

<210> SEQ ID NO 9
<211> LENGTH: 5
<212> TYPE: PRT
<213> ORGANISM: Artificial Sequence
<220> FEATURE:
```

<223> OTHER INFORMATION: HCDR1 of humanized 99 antibody

<400> SEQUENCE: 9

Asn Tyr Gly Met Asn
1               5

<210> SEQ ID NO 10
<211> LENGTH: 17
<212> TYPE: PRT
<213> ORGANISM: Artificial Sequence
<220> FEATURE:
<223> OTHER INFORMATION: HCDR2 of humanized 99 antibody

<400> SEQUENCE: 10

Trp Ile Asn Thr Lys Ile Gly Glu Pro Thr Tyr Ala Gln Lys Phe Gln
1               5                   10                  15

Gly

<210> SEQ ID NO 11
<211> LENGTH: 4
<212> TYPE: PRT
<213> ORGANISM: Artificial Sequence
<220> FEATURE:
<223> OTHER INFORMATION: HCDR3 of humanized 99 antibody

<400> SEQUENCE: 11

Leu Leu Asp Tyr
1

<210> SEQ ID NO 12
<211> LENGTH: 17
<212> TYPE: PRT
<213> ORGANISM: Artificial Sequence
<220> FEATURE:
<223> OTHER INFORMATION: LCDR1 of humanized 99 antibody

<400> SEQUENCE: 12

Arg Ala Ser Gln Ser Val Leu Tyr Ser Ser Asn Gln Lys Asn Tyr Leu
1               5                   10                  15

Ala

<210> SEQ ID NO 13
<211> LENGTH: 7
<212> TYPE: PRT
<213> ORGANISM: Artificial Sequence
<220> FEATURE:
<223> OTHER INFORMATION: LCDR2 of humanized 99 antibody

<400> SEQUENCE: 13

Trp Ala Ser Ser Leu Gln Ser
1               5

<210> SEQ ID NO 14
<211> LENGTH: 8
<212> TYPE: PRT
<213> ORGANISM: Artificial Sequence
<220> FEATURE:
<223> OTHER INFORMATION: LCDR3 of humanized 99 antibody

<400> SEQUENCE: 14

His Gln Tyr Leu Ser Ser Tyr Thr
1               5

<210> SEQ ID NO 15
<211> LENGTH: 113

<212> TYPE: PRT
<213> ORGANISM: Artificial Sequence
<220> FEATURE:
<223> OTHER INFORMATION: Heavy chain variable region of humanized 99
      antibody

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Lys Ile Gly Glu Pro Thr Tyr Ala Gln Lys Phe
    50                  55                  60

Gln Gly Arg Val Thr Met Thr Arg Asp Lys Ser Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Leu Asp Tyr Trp Gly Gln Gly Thr Leu Val Thr Val Ser
            100                 105                 110

Ser

<210> SEQ ID NO 16
<211> LENGTH: 113
<212> TYPE: PRT
<213> ORGANISM: Artificial Sequence
<220> FEATURE:
<223> OTHER INFORMATION: Light chain variable region of humanized 99
      antibody

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Leu Tyr Ser
            20                  25                  30

Ser Asn Gln Lys Asn Tyr Leu Ala Trp Tyr Gln Gln Lys Pro Gly Lys
        35                  40                  45

Ser Pro Lys Leu Leu Ile Tyr Trp Ala Ser Ser Leu Gln Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys His Gln
                85                  90                  95

Tyr Leu Ser Ser Tyr Thr Phe Gly Gln Gly Thr Lys Val Glu Ile Lys
            100                 105                 110

Arg

<210> SEQ ID NO 17
<211> LENGTH: 16
<212> TYPE: PRT
<213> ORGANISM: Artificial Sequence
<220> FEATURE:
<223> OTHER INFORMATION: Fibrinogen Bbeta 231-246

<400> SEQUENCE: 17

Cys Asn Ile Pro Val Val Ser Gly Lys Glu Cys Glu Glu Ile Ile Arg
1               5                   10                  15

-continued

```
<210> SEQ ID NO 18
<211> LENGTH: 15
<212> TYPE: PRT
<213> ORGANISM: Artificial Sequence
<220> FEATURE:
<223> OTHER INFORMATION: Fibrinogen gamma 232-246

<400> SEQUENCE: 18

Lys Asn Trp Ile Gln Tyr Lys Glu Gly Phe Gly His Leu Ser Pro
1               5                   10                  15
```